US008017144B2

(12) United States Patent
Dumont et al.

(10) Patent No.: US 8,017,144 B2
(45) Date of Patent: Sep. 13, 2011

(54) CONTROLLED RELEASE POLYMERIC COMPOSITIONS OF BONE GROWTH PROMOTING COMPOUNDS

(75) Inventors: Francis Dumont, Ledyard, CT (US); Richard L. Dunn, Fort Collins, CO (US); Scott A. Jeffers, Fort Collins, CO (US); Richard W. Korsmeyer, Old Lyme, CT (US); Mei Li, Westerly, RI (US); Vishwas M. Paralkar, Madison, CT (US); Mingxing Zhou, Fort Collins, CO (US)

(73) Assignee: Pfizer Inc., Madison, NJ (US)

( * ) Notice: Subject to any disclaimer, the term of this patent is extended or adjusted under 35 U.S.C. 154(b) by 128 days.

(21) Appl. No.: 12/257,803

(22) Filed: Oct. 24, 2008

(65) Prior Publication Data
US 2009/0169595 A1  Jul. 2, 2009

Related U.S. Application Data

(63) Continuation of application No. 10/303,590, filed on Nov. 25, 2002, now abandoned.

(60) Provisional application No. 60/337,255, filed on Nov. 30, 2001.

(51) Int. Cl.
*A61F 2/02* (2006.01)
(52) U.S. Cl. ........................................ 424/426
(58) Field of Classification Search .................. None
See application file for complete search history.

(56) References Cited

U.S. PATENT DOCUMENTS
6,143,314 A  11/2000  Chandrashekar et al. .... 424/426

FOREIGN PATENT DOCUMENTS

| EP | 0950403 | 10/1999 |
|----|---------|---------|
| WO | WO 9528124 | 10/1995 |
| WO | WO 9621427 | 7/1996 |
| WO | WO 9827962 | 7/1998 |
| WO | WO 9828264 | 7/1998 |
| WO | WO 9919300 | 4/1999 |

OTHER PUBLICATIONS

Bonnarens, et al., *Journal of Orthopaedic Research*, Production of a standard closed fracture in laboratory animal bone, (1984), vol. 2(1), pp. 97-101.
Coonts, et al., *Journal of Biomedical Materials Research*, Biodegradation and biocompatibility of a guided tissue regeneration barrier membrane formed from a liquid polymer material (1998), vol. 42(2), pp. 303-311.
Dunn, et al., *Modified-Release Drug Delivery Technology*, The atrigel drug delivery system, (2002), pp. 647-655.
Joyce, et al., Journal of Cell Biology, Transforming growth Factor-β and the Initiation of Chodrogenesis and Osteogenesis in the Rat Femur, (1990), vol. 110, pp. 2195-2207.
Royals, et al., *Journal of Biomedical Materials Research*, Biocompatibility of a biodegradable in situ forming implant. (1999), vol. 45(3), pp. 231-239.

*Primary Examiner* — Carlos Azpuru
(74) *Attorney, Agent, or Firm* — Ram W. Sabnis

(57) ABSTRACT

The present invention is directed to an improved system for controlled release of a bone growth promoting compound and to a flowable composition for its formation. The flowable composition is composed of a bone growth promoting compound, a thermoplastic polymer and an organic solvent. The flowable composition is capable of forming a biodegradable and/or bioerodible microporous, solid polymer matrix. The matrix is useful as an implant in patients (humans and animals) for delivery of a bone growth promoting compound to certain tissues.

10 Claims, No Drawings

CONTROLLED RELEASE POLYMERIC COMPOSITIONS OF BONE GROWTH PROMOTING COMPOUNDS

This is a continuation application of U.S. Ser. No. 10/303,590, filed on Nov. 25, 2002, which claims priority from U.S. Provisional Application No. 60/337,255, filed on Nov. 30, 2001. The entire disclosure of the above parent applications are fully incorporated herein by reference thereto.

FIELD OF THE INVENTION

The invention is directed to an improved system for the controlled release of a bone growth promoting compound and to a flowable composition for its formation. The flowable composition is composed of a thermoplastic polymer, a bone growth promoting compound and an organic solvent. The flowable composition is capable of forming a biodegradable and/or bioerodible microporous, solid polymer matrix. The matrix is useful as an implant in patients (humans and animals) for delivery of a bone growth promoting compound to bone tissues.

BACKGROUND OF THE INVENTION

Biodegradable polymers are useful in many medical applications, especially drug delivery devices. Many of the biodegradable polymers used are of the thermoplastic type. Polymers made of thermoplastic resins typically liquify or soften at elevated temperatures and resolidify upon cooling. This type of polymer is generally formed into the desired structure for use as sutures, surgical clips, staples, implants and the like, prior to insertion into the body. Once inserted into the body, these polymers retain their shape.

For drug delivery devices, the drug is generally incorporated into the polymeric composition and formed into the desired shape outside the body. This solid implant is then typically inserted into the body of a human, animal, bird or the like through an incision. Alternatively, small discrete particles composed of these polymers can be injected into the body by a syringe. Preferably, however, certain of these polymers can be injected via syringe as a flowable polymeric composition.

Flowable polymeric compositions for use as biodegradable controlled release drug delivery systems are described in the patent literature, e.g., U.S. Pat. Nos. 4,938,763; 5,077,049; 5,324,519; 5,632,727; 5,599,552; 5,702,716; 5,487,897; 5,660,849; 5,278,201; 5,198,220; 5,447,725; 5,242,910; 5,733,950; 5,739,176; 5,945,115; 5,744,153; 5,759,563; 5,660,849; and 6,143,314.

These compositions are administered to the body in a flowable physical state, typically via syringe. Once in the body the composition transforms into a solid. One type of polymeric composition consists of a nonreactive thermoplastic polymer or copolymer dissolved or dispersed in an organic solvent. This polymeric solution is placed into the body where the polymer gels or precipitatively solidifies upon the dissipation or diffusion of the solvent into the surrounding body tissues. Also, improved polymeric compositions that form a solid matrix in situ thereby forming an implant for sustained release of a medicament over a desired period of time are described in the patent literature.

An example of a commercially available product that utilizes this technology is the ATRIDOX™ product which is a subgingival controlled-release product composed of a two syringe mixing system. Syringe A contains 450 mg of the ATRIGEL® Delivery System, which is a bioabsorbable, flowable polymeric formulation composed of 36.7% poly (DL-lactide)(PLA) dissolved in 63.3% N-methyl-2-pyrrolidone (NMP). Syringe B contains the antibiotic doxycycline hyclate which is equivalent to 42.5 mg doxycycline.

K. P. Andriano et al., J. Biomed. Mater. Res. (Appl. Biomater.), 53: 36-43 (2000), disclose preliminary in vivo studies on the osteogenic potential of bone morphogenetic proteins delivered from an absorbable puttylike polymer matrix. R. L. Dunn et al., Portland Bone Symposium 1999, Oregon Health Sciences University, pages 522 to 528, studied the osteoinductivity of bone morphogenetic proteins delivered from an absorbable putty-like matrix.

The optimal control of release rate of certain bone growth promoting compounds, especially certain small molecule, is a never-ending quest for sustained release implants including but not limited to the flowable compositions. Consequently, there is the need for a flowable composition in which the rate of delivery of certain bone growth promoting compounds can be more readily controlled, especially for a compound which requires sustained release over a longer time period.

SUMMARY OF THE INVENTION

It is an object of the present invention to provide improved polymeric compositions in which the rate of release of a bone growth promoting compound is balanced against the rate of degradation of the polymer. It is a further object of the present invention to provide improved polymeric compositions which form an implant in situ that degrades quickly enough so as to not impede bone growth at the desired site.

The present invention provides the following:

A pharmaceutical composition suitable for in situ formation of an implant in a patient comprising:

(a) a pharmaceutically acceptable, biodegradable thermoplastic polymer or copolymer that is insoluble in aqueous or body fluid;

(b) a biocompatible organic solvent which solubilizes the thermoplastic polymer, is dispersible in situ in body fluid, is highly soluble in water and is capable of dissipating from the polymer system into surrounding tissue fluid whereupon the thermoplastic polymer forms the implant; and (c) a therapeutically effective amount of a compound or a pharmaceutically acceptable salt thereof selected from the group consisting of:

(3-(((4-tert-butyl-benzyl)-(pyridine-3-sulfonyl)-amino)-methyl)-phenoxy)-acetic acid;

7-[(4-butyl-benzyl)-methanesulfonyl-amino]-heptanoic acid; and

7-{[2-(3,5-dichloro-phenoxy)-ethyl]-methanesulfonyl-amino}-heptanoic acid.

More particularly, the present invention provides the above composition wherein the composition forms a controlled release implant at or near the site of local administration. Also, the present invention provides the above composition wherein the composition forms a controlled release implant at or near the site of the bone fracture, bone injury or bone defect.

More particularly, the present invention provides the above composition wherein the compound is the sodium salt of (3-(((4-tert-butyl-benzyl)-(pyridine-3-sulfonyl)-amino)-methyl)-phenoxy)-acetic acid. Also, the present invention provides the above composition wherein the compound is the free acid of (3-(((4-tert-butyl-benzyl)-(pyridine-3-sulfonyl)-amino)-methyl)-phenoxy)-acetic acid.

More particularly, the present invention provides the above composition wherein the amount of the compound is between about 5 to about 50 mgA/ml of the composition. Even more particularly, the present invention provides the above composition wherein the amount of the compound is about 5, 10 or 50 mgA/ml of the composition.

More particularly, the present invention provides the above composition wherein the polymer is selected from the group consisting of polylactides, polyglycolides and copolymers thereof. More particularly, the present invention provides the above composition wherein the copolymer has an inherent viscosity of about 0.20 dl/g to about 0.40 dl/g. Even more particularly, the present invention provides the above composition wherein the copolymer has an inherent viscosity of about 0.20 dl/g.

More particularly, the present invention provides the above composition wherein the copolymer is poly-lactic-co-glycolic acid (PLGH). Even more particularly, the present invention provides the above composition wherein the ratio of lactic acid to glycolic acid is about 1 to about 1.

More particularly, the present invention provides the above composition wherein the copolymer is polyethylene glycol (PEG) end-capped poly-lactic-co-glycolic acid (PLGH). Even more particularly, the present invention provides the above composition wherein the weight % of PEG to PLGH is between about 3 to about 5%.

More particularly, the present invention provides the above composition wherein the solvent is N-methyl-2-pyrrolidone (NMP). Even more particularly, the present invention provides the above composition wherein the copolymer is poly-lactic-co-glycolic acid (PLGH) and wherein the solvent is N-methyl-2-pyrrolidone (NMP). The present invention provides such composition wherein the weight percentage of PLGH to NMP in solution is between about 30% and about 60% of PLGH to between about 70% and about 40% of NMP. Even more particularly, the present invention provides the above composition wherein the weight percentage of PLGH to NMP in solution is selected from the following: about 37% PLGH to about 63% NMP; about 45% PLGH to about 55% NMP; about 50% PLGH to about 50% NMP; and about 55% PLGH to about 45% NMP. Most particularly, the present invention provides the above composition wherein the weight percentage of PLGH to NMP in solution is about 50% PLGH to about 50% NMP.

In addition, the present invention provides a pharmaceutical kit suitable for in situ formation of a biodegradable implant in the body of a patient, which comprises:

A) a device containing a compound or a pharmaceutically acceptable salt thereof selected from the group consisting of:
(3-(((4-tert-butyl-benzyl)-(pyridine-3-sulfonyl)-amino)-methyl)-phenoxy)-acetic acid;
7-[(4-butyl-benzyl)-methanesulfonyl-amino]-heptanoic acid; and
7-{[2-(3,5-dichloro-phenoxy)-ethyl]-methanesulfonyl-amino}-heptanoic acid; and B) a device containing a flowable composition of a biodegradable, biocompatible, pharmaceutically acceptable thermoplastic polymer that is insoluble in aqueous or body fluid and a pharmaceutically acceptable solvent that is dispersible in situ in body fluid and is highly water soluble, wherein the concentrations and formulas of the polymer and the solvent in the flowable composition are effective to form an implant in situ when the flowable composition contacts body fluid:

C) wherein the devices have an outlet for the compound or the flowable composition, an ejector for expelling the compound or the flowable composition through the outlet and a hollow tube fitted to the outlet; and wherein the contents of the two devices are mixed together immediately prior to delivering the contents of the device containing the mixture into the body of the patient.

More particularly, the present invention provides the above pharmaceutical kit wherein the concentrations and formulas of the polymer and the solvent are effective to form a space filling implant in the body of the patient.

More particularly, the present invention provides the above pharmaceutical kit wherein the polymer is selected from the group consisting of polylactides and copolymers thereof with glycolide. Even more particularly, the present invention provides the above pharmaceutical kit wherein the copolymer is poly-lactic-co-glycolic acid (PLGH). Even more particularly, the present invention provides the above pharmaceutical kit wherein the ratio of lactic acid to glycolic acid is about 1 to about 1.

More particularly, the present invention provides the above pharmaceutical kit wherein the solvent is N-methyl-2-pyrrolidone (NMP). More particularly, the present invention provides the above pharmaceutical kit wherein the compound is in the lyophilized form.

Also, the present invention provides a method of forming an implant in-situ, in a living body, comprising the steps of:
(a) dissolving a non-reactive, water-insoluble biodegradable polymer in a biocompatible, highly water soluble organic solvent that is dispersible in body fluid in situ to form a flowable composition;
(b) adding an effective amount of a compound to the flowable composition to provide a pharmaceutical composition;
(c) placing the pharmaceutical composition within the body; and
(d) allowing the solvent to dissipate to produce a solid or gel implant which releases the compound by diffusion, erosion or a combination of diffusion and erosion as the implant biodegrades;

wherein the compound or a pharmaceutically acceptable salt thereof is selected from the group consisting of:
(3-(((4-tert-butyl-benzyl)-(pyridine-3-sulfonyl)-amino)-methyl)-phenoxy)-acetic acid;
7-[(4-butyl-benzyl)-methanesulfonyl-amino]-heptanoic acid; and
7-{[2-(3,5-dichloro-phenoxy)-ethyl]-methanesulfonyl-amino}-heptanoic acid;
wherein the polymer is selected from the group consisting of polylactides and copolymers thereof with glycolide; and
wherein the solvent is N-methyl-2-pyrrolidone (NMP).

More particularly, the present invention provides the above method wherein the copolymer is poly-lactic-co-glycolic acid (PLGH). More particularly, the present invention provides the above method which further comprises delivering said liquid in-situ through a syringe. More particularly, the present invention provides the above method wherein the implant is formed at or near a bone fracture, bone defect or bone injury in the body. Also, the present invention provides a biodegradable drug delivery implant for a body produced according to the above method.

In addition, the present invention provides a kit for achieving a therapeutic effect in a mammal which has been prescribed the joint administration of the ingredients designated as (1) and (2) below, each ingredient forming a portion of said kit, comprising in association:
(1) a therapeutically effective amount of an active ingredient, said active ingredient being (3-(((4-tert-butyl-benzyl)-(pyridine-3-sulfonyl)-amino)-methyl)-phenoxy)-acetic acid; 7-[(4-butyl-benzyl)-methanesulfonyl-amino]-heptanoic acid; or 7-{[2-(3,5-dichloro-phenoxy)-ethyl]-methanesulfonyl-amino}-heptanoic acid; or a pharmaceutically acceptable salt thereof and a pharmaceutically acceptable carrier or diluent in a first unit dosage form;

(2) a flowable composition of a biodegradable, biocompatible, pharmaceutically acceptable thermoplastic polymer that is insoluble in aqueous or body fluid and a pharmaceutically acceptable, highly water soluble solvent that is dispersible in situ in body fluid, wherein the concentrations and formulas of the polymer and the solvent in the composition are effective to form an implant in situ when said composition contacts body fluid; in a second unit dosage form; and (3) directions for the administration of the ingredients (1) and (2) in a manner to achieve the desired therapeutic effect.

More particularly, the present invention provides the above kit wherein the active ingredient is the sodium salt of (3-(((4-tert-butyl-benzyl)-(pyridine-3-sulfonyl)-amino)-methyl)-phenoxy)-acetic acid. More particularly, the present invention provides the above kit wherein the active ingredient is the free acid of (3-(((4-tert-butyl-benzyl)-(pyridine-3-sulfonyl)-amino)-methyl)-phenoxy)-acetic acid.

More particularly, the present invention provides the above kit wherein the polymer is selected from the group consisting of polylactides, polyglycolides and copolymers thereof. Even more particularly, the present invention provides the above kit wherein the polymer is selected from the group consisting of polylactides and copolymers thereof with glycolide. Even more particularly, the present invention provides the above kit wherein the copolymer is poly-lactic-co-glycolic acid (PLGH). Even more particularly, the present invention provides the above kit wherein the ratio of lactic acid to glycolic acid is about 1 to about 1.

More particularly, the present invention provides the above kit wherein the solvent is N-methyl-2-pyrrolidone (NMP). Also, the present invention provides the above kit wherein the compound is in the lyophilized form.

The present invention is directed to a polymer system for specific bone growth promoting compounds, a method for therapeutic treatment using such polymer system and a precursor of such polymer system, a flowable composition.

The present invention provides a flowable composition that provides sustained release at the local site of injection (e.g., bone fracture site, bone defect site, bone injury site) by forming a biodegradable solid or gel implant. More particularly, the present invention provides a composition and method for delivering a bone growth promoting compound in a slow-release biodegradable polymer based delivery system, which is preferably injectable.

The polymer system is a microporous, solid or gel matrix of a biocompatible, biodegradable thermoplastic polymer and a bone growth promoting compound. The system of the present invention provides for optimal control of the rate and extent of release of the bone growth promoting compound from the matrix. The flowable composition contains an organic solvent, a biocompatible, biodegradable thermoplastic polymer and a bone growth promoting compound.

The polymer system is formed by applying the flowable composition to either of two gelation media: a) body fluid that is internal to the body, and b) a water medium that is external to the body. After application, the flowable composition gels or coagulates to form the polymer system. Administration of the flowable composition directly into the body forms in situ the polymer system. External addition of the flowable composition to a water medium forms the polymer system outside the body. The solid implantable polymer system formed outside the body can then be surgically placed into the body. In all embodiments and applications, the polymer system is substantially insoluble in water, water solutions and body fluid.

The process by which the polymer system is formed in part is responsible for development of the rate and release control. Interaction of the flowable composition with body fluid in situ in the body to coagulate or gel the composition into the polymer system at least in part causes the desired controlled release profile as a function of the variation of the below-mentioned parameters and components. Simple combination of these components without passage through the flowable composition will not develop the controlled release profile of the present invention. When the flowable composition is contacted by body fluid in situ, the organic solvent diffuses into the surrounding medium (body fluids) and the polymer coagulates or gels to form the solid or gel matrix (polymer system). Because the body fluid contains lipophilic components and dynamically flows around the flowable composition, the coagulation or gelling occurs when the organic solvent has a water solubility ranging from highly soluble to insoluble.

When the composition of the present invention is placed in the body, it is retained locally at the site of the fracture, defect or injury. The resulting polymer system may adopt the shape of the bone fracture, defect or injury into which the composition is placed.

Pursuant to the parameters and conditions of the present invention, the polymer system can control the sustained release of a bone growth promoting compound in vivo. In particular, the rate and extent of release of the bone growth promoting compound from the polymer system of the present invention are controlled over a narrow range of speeds and amounts. This control is accomplished by variation of: (a) the polymer type and molecular weight, (b) the concentration of the polymer, (c) the concentration of the bone growth promoting compound, and (d) the form of the bone growth promoting compound. Preferably, the rate and extent of release of the bone growth promoting compound from the polymer system according to the present invention can be controlled by varying: (1) the type and molecular weight of the polymer or polymers, and/or (2) the concentration of the polymer.

More preferably, the control is accomplished by varying the molecular weight of the polymer. In preferred embodiments, the rate of release increases as polymer molecular weight decreases.

The method of the present invention is based upon the therapeutic effect of the in situ controlled release of the bone growth promoting compound from the polymer system. The implantation of the flowable composition occurs at or near the site of the bone fracture, bone defect or bone injury in the body of a patient in need of therapeutic treatment. For example, it may be implanted in the bone fracture so that it adapts and conforms to the shape of the fracture. Preferably, it is implanted in the soft tissue, such as muscle or fat, at or near the site of the bone fracture, defect or injury. The composition can be administered to the implant site by any suitable method for applying a flowable composition, as for example, by means of a syringe, needle, cannula or catheter. The polymer system preformed as an implant can be inserted by known surgical techniques.

DETAILED DESCRIPTION OF THE INVENTION

The present invention relates to a polymer system for the controlled delivery of a bone growth promoting compound, a flowable composition for producing such system, and a method for use of such a system in therapeutic treatment. The polymer system of the present invention is advantageous in that it can be manipulated to control the amount of bone growth promoting compound released and the rate at which it is released in vivo.

The present invention provides an injectable, flowable composition that provides sustained release at the local site of the injection (e.g., bone fracture site, bone defect site, bone injury site) by forming a biodegradable solid or gel depot, matrix or implant.

More particularly, the present invention provides a composition and method for delivering a bone growth promoting compound in a slow-release biodegradable polymer based delivery system.

The polymer based delivery system contains a bone growth promoting compound dissolved or dispersed in biodegradable, thermoplastic polymer solution or dispersion in an organic solvent. Upon injection of the flowable composition, the organic solvent diffuses away from the injection site, causing the polymer to precipitate or gel; thereby entrapping the compound in a sustained-release depot. The compound is subsequently released by diffusion from, and erosion of, the polymeric matrix. The polymeric matrix slowly erodes by hydrolysis and eventually disappears from the site of administration. The molecular weight and concentration of the polymer can control the in vivo release of the compound as well as the degradation rate of the matrix.

The polymer based delivery system of the present invention provides sustained release of a bone growth promoting compound in vivo for a sustained period of time with minimum or reduced burst that is efficacious in promoting bone growth in a patient in need thereof. A large burst of compound would result in poor local toleration due to local effects of the compound (e.g., irritation) and would minimize the amount of compound available for efficacy. The advantages of the compositions of the present invention are that they minimize or reduce the initial burst but still deliver compound at efficacious levels for a sustained period of time upon a single local injection.

The polymer system is prepared by contacting the flowable composition with a gelation medium to coagulate or gel the composition into a solid, microporous polymeric matrix or a gel polymeric matrix. The flowable composition contains a thermoplastic polymer or copolymer in combination with a suitable solvent. The polymers or copolymers, which form the body of the matrix, are substantially insoluble, preferably essentially completely insoluble, in water and body fluids. The insolubility of the matrix body enables it to function as a single site for the controlled release of the bone growth promoting compound. The polymers or copolymers also are biocompatible and biodegradable and/or bioerodible within the body of an animal, e.g., mammal. The biodegradation enables the patient to metabolize the polymer matrix so that it can be excreted by the patient without the need for further surgery to remove it. Because the flowable composition and polymer system are biocompatible, the insertion process and the presence of the polymer system within the body do not cause substantial tissue irritation or necrosis at the implant site. The composition of the present invention is administered as a flowable composition directly into body tissues, e.g., soft tissue at or near the bone defect or bone fracture site, wherein an implant of the polymer system is formed in situ.

The term "patient" means an animal, such as a human, a companion animal, such as a dog, cat and horse, and livestock, such as cattle, swine and sheep. Particularly preferred patients are mammals, including both males and females, with humans being even more preferred.

The bone growth promoting compounds of the present invention are the following:

(3-(((4-tert-butyl-benzyl)-(pyridine-3-sulfonyl)-amino)-methyl)-phenoxy)-acetic acid, including its free acid and its pharmaceutically acceptable salts, such as the sodium salt. This compound and pharmaceutically acceptable salts thereof may be prepared according to the synthetic methodologies described in published International patent application WO 99/19300, which are incorporated by reference herein.

7-[(4-butyl-benzyl)-methanesulfonyl-amino]-heptanoic acid and its pharmaceutically acceptable salts. This compound and pharmaceutically acceptable salts thereof may be prepared according to the synthetic methodologies described in published International patent application WO 98/28264, which are incorporated by reference herein.

7-{[2-(3,5-dichloro-phenoxy)-ethyl]-methanesulfonyl-amino}-heptanoic acid and its pharmaceutically acceptable salts. This compound and pharmaceutically acceptable salts thereof may be prepared according to the synthetic methodologies described in published International patent application WO 98/28264; which are incorporated by reference herein.

The above three compounds are capable of promoting growth and survival of bone cells and tissues, or augmenting the activity of functioning bone cells and tissues and bone marrow and the like.

Suitable thermoplastic polymers for incorporation into the solid matrix of the controlled release polymer system are solids, pharmaceutically compatible and biodegradable by cellular action and/or by the action of body fluids. Examples of appropriate thermoplastic polymers include polyesters of diols and dicarboxylic acids or of hydroxycarboxylic acids, such as polylactides, polyglycolides and copolymers thereof. More preferably the polymer is the copolymer, poly-lactic-co-glycolic acid (abbreviated PLGH), which upon hydrolysis, produces lactic and glycolic acid. The burst of release of this copolymer can be minimized further by the addition of polyethylene glycol (PEG) to form the PEG end-capped PLGH.

Preferred materials for use in the present invention are the polylactides, polyglycolides and copolymers thereof. These polymers can be used to advantage in the polymer system in part because they show excellent biocompatibility. They produce little, if any, tissue irritation, inflammation, necrosis or toxicity. In the presence of water, these polymers produce lactic and glycolic acid, respectively, which are readily metabolized by the body. The polylactides can also incorporate glycolide monomer to enhance the resulting polymer's degradation. These polymers can also be used to advantage in the polymer system of the present invention because they effectively control the rate of release of the bone growth promoting compound from the polymer system and because they result in the local retention of the bone growth promoting compound at the site of the bone fracture, defect or injury. These polymers are also preferred because they degrade quickly enough from the site of the bone fracture, defect or injury so as to not impede bone growth at the site of the bone fracture, defect or injury.

The solubility or miscibility of a thermoplastic polymer in the organic solvent of the composition will vary according to factors such as crystallinity, hydrophilicity, capacity for hydrogen bonding and molecular weight of the polymer. Consequently, the molecular weight and the concentration of the polymer in the solvent are adjusted to achieve desired miscibility, as well as a desired release rate for the incorporated bone growth promoting compound.

According to the practice of the present invention, the flowable composition of thermoplastic polymer, solvent and the bone growth promoting compound is a stable flowable substance. In the present invention, a homogenous solution of the bone growth promoting compound in an organic solvent preferably results. The thermoplastic polymer is substantially soluble in the organic solvent. Upon placement of the flowable composition into the body, the solvent will dissipate and the polymer will solidify or gel to form the polymer system having the bone growth promoting compound within a solid or gel polymeric matrix.

While not intending to limit the present invention to a specific mechanism of action, it has been discovered that the molecular weight of the polymer used in the present invention distinctly affects the rate of release of the bone growth promoting compound and the rate of degradation of the polymer from the site of the bone fracture, defect or injury as long as the flowable composition has been used as an intermediate.

For certain preferred polymers for use in the present invention, the molecular weight of the polymer or copolymer is adjusted to be within a range of about 0.2 to about 0.4 inherent viscosity (I.V. in deciliters/g) for effective sustained release of the bone growth promoting compound. The typical rate of release of the incorporated bone growth promoting compound occurs at an I.V. of about 0.2 (about 8,000 to about 16,000 molecular weight) or about 0.3 (about 23,000 to about 45,000 molecular weight) but can vary depending on the particular components of the composition. For most systems, it is preferred to adjust the molecular weight of the polymer to about 0.2 I.V. for an effective sustained release of the bone growth promoting compound. The unit of measure for the molecular weight is daltons.

For a poly(DL-lactide) or a lactide-co-glycolide polymer system, the desired molecular weight range is about 0.2 to about 0.4 I.V., with an I.V. of about 0.2 being most preferred. The molecular weight of a polymer can be varied by any of a variety of methods. The choice of method is typically determined by the type of polymer composition. The preferred polymers for use in the present invention are commercially available.

Highly preferred thermoplastic polymers for use in the present invention are the following: PLGH copolymer with 1:1 ratio of lactic and glycolic acid with an inherent viscosity of about 0.2 dl/g (commercially available from Boehringer Ingelheim as Copolymer RESOMER® RG 502H) (about 12,000 molecular weight); PLGH copolymer with 1:1 ratio of lactic and glycolic acid with an inherent viscosity of about 0.3 dl/g (commercially available from Boehringer Ingelheim as Copolymer RESOMER® RG 503H)(about 37,000 molecular weight); PLGH copolymer with 1:1 ratio of lactic and glycolic acid with an inherent viscosity of about 0.4 dl/g (commercially available from Boehringer Ingelheim as Copolymer RESOMER® RG 504H) (about 47,000 molecular weight); and polyethylene glycol (PEG) end-capped PLGH copolymer with 1:1 ratio of lactic and glycolic acid with an inherent viscosity of about 0.79 dl/g (commercially available from Boehringer Ingelheim as PLG-PEG) (about 52,000 molecular weight).

By appropriate choice of the polymer molecular weight and viscosity, the rate and extent of release of the bone growth promoting compound of the present invention from the polymer system can be varied from very fast to very slow. For example, according to the present invention, the release rate of the bone growth promoting compound, (3-(((4-tert-butyl-benzyl)-(pyridine-3-sulfonyl)-amino)-methyl)-phenoxy)-acetic acid, sodium salt, can be slowed to produce substantially complete release of the compound within about seven days. With the use of a greater viscosity of polymer according to the present invention, the period of time can be increased to about fourteen days. The desired release rate of the bone growth promoting compound will depend on several factors, such as the species of animal being treated as well as the specific condition being treated.

The concentration of the polymer in the system can also be varied to adjust the release rate of the incorporated bone growth promoting compound. It has been discovered that the more dilute the polymer concentration, the more readily the bone growth promoting compound will be released. This effect can be used in combination with other methods to more effectively control the release of the incorporated bone growth promoting compound as desired. For example, by adjusting the concentration of the polymer and the bone growth promoting compound, if desired, a wide range of release rates can be obtained The solvents used in the thermoplastic compositions of the present invention are preferably pharmaceutically acceptable, biocompatible and will dissipate into body fluid in situ such that they may be classed as having a solubility in water ranging from highly soluble to insoluble. Preferably, they cause relatively little, if any, tissue irritation or necrosis at the site of the injection and implantation. Preferably, the solvent may have at least a minimal degree of water solubility. When the organic solvent is water insoluble or is minimally soluble in water, the solvent will slowly disperse from the flowable polymeric composition. The result will be an implant that during the course of its life may contain a varying amount of residual solvent. Especially preferably, the organic solvent has a moderate to high degree of water solubility so that it will facilely disperse from the polymeric composition into the body fluids. Most preferably, the solvent disperses rapidly from the polymeric composition so as to quickly form a solid implant. Concomitant with the dispersion of solvent, the thermoplastic polymer coagulates or gels into the solid polymer system. Preferably, as the thermoplastic polymer coagulates, the solvent dispersion causes pore formation within the polymer system. As a result, the flowable composition containing thermoplastic polymer, solvent and bone growth promoting compound will form a porous solid polymer system. Also, when the solvent is slightly water soluble or is water insoluble, the solvent dispersion may result in the formation of a solid porous implant, or if some solvent remains with the implant, the result may be formation of a gel implant having few or no pores.

Suitable solvents include those liquid organic compounds meeting the foregoing criteria. The preferred solvent for use in the present invention is N-methyl-2-pyrrolidone (NMP) due, at least in part, to its solvating ability and its biocompatibility.

The solvents for the thermoplastic polymer flowable compositions of the present invention are chosen for compatibility and appropriate solubility of the polymer and solvent. Lower molecular weight thermoplastic polymers will normally dissolve more readily in the solvents than high molecular weight polymers. As a result, the concentration of a thermoplastic polymer dissolved in the various solvents differs depending upon type of polymer and its molecular weight. Conversely, the higher molecular weight thermoplastic polymers will tend to coagulate, gel or solidify faster than the very low molecular weight thermoplastic polymers. Moreover, the higher molecular weight polymers tend to give higher solution viscosities than the low molecular weight materials. Thus, for advantageous injection efficiency, in addition to advantageous release rate, the molecular weight and the concentration of the polymer in the solvent are controlled.

Upon formation of the polymer system from the flowable composition, the bone growth promoting compound becomes incorporated into the polymer matrix. After insertion of the flowable composition to form in situ the polymer system, the bone growth promoting compound will be released from the matrix into the adjacent tissues or fluids by diffusion and polymer degradation mechanisms. Manipulation of these mechanisms also can influence the release of the bone growth promoting compound into the surroundings at a controlled rate. For example, the polymer matrix can be formulated to degrade after an effective and/or substantial amount of the bone growth promoting compound is released from the matrix. Thus, the release of the bone growth promoting compound from the matrix can be varied by, for example, the solubility of the bone growth promoting compound in water, the distribution of the bone growth promoting compound within the matrix, or the size, shape, porosity, solubility and biodegradability of the polymer matrix, among other factors. The release of the bone growth promoting compound from the matrix is controlled relative to its inherent rate by varying the polymer molecular weight to provide a desired duration and rate of release.

The polymer system is formulated to contain a bone growth promoting compound in an amount effective to provide a desired biological, physiological and/or therapeutic effect. More particularly, the polymer system of the present invention is formulated to contain a bone growth promoting compound in an amount effective to promote the growth and survival of bone cells and tissues, and/or augment the activity of functioning bone cells and tissues and bone marrow and the like.

The "therapeutically effective amount" of a bone growth promoting compound incorporated into the polymeric composition of the present invention depends on a variety of factors, such as the desired release profile, the concentration of bone growth promoting compound required for a desired biological effect, and the period of time over which the bone growth promoting compound needs to be released for desired treatment. Ultimately, this amount is determined by the human or animal patient's physician or veterinarian, respectively, who will apply his experience and wisdom in prescribing the appropriate kind and amount of bone growth promoting compound to provide therapy for the patient. There is generally no critical upper limit on the amount of bone growth promoting compound incorporated into the polymer solution. The only limitation is a physical limitation for advantageous application, i.e., the bone growth promoting compound should not be present in such a high concentration that the solution or dispersion viscosity is too high for injection. The lower limit of the bone growth promoting compound incorporated into the polymer system typically depends only on the activity of the bone growth promoting compound and the period of time desired for treatment.

Preferably, a therapeutically effective amount for the bone growth treatment for the bone growth promoting compounds of the present invention range between about 0.001 to about 100 mg/kg/day, with an especially preferred amount being about 0.01 to about 10 mg/kg/day.

Administration of the flowable composition of the present invention ultimately will be accomplished according to the wisdom and protocol of the patient's attending health care professional such as a physician, or if appropriate, a DVM. Choice of the particular composition will depend upon the condition to be treated, which choice will be made by the attending health care professional. For example, with hard tissue such as bone, the biodegradable polymer containing a bone growth promoting compound supports the growth of new bone cells. These new bone cells eventually replace the degrading polymer.

For example, a preferred dosage form of the bone growth promoting compound, (3-(((4-tert-butyl-benzyl)-(pyridine-3-sulfonyl)-amino)-methyl)-phenoxy)-acetic acid, is a lyophile of the sodium salt to be reconstituted with a solution of PLGH in NMP before administration. The dosage form, consisting of the lyophilized compound in one syringe (syringe A) and a solution of PLGH in NMP in a second syringe (syringe B), is known as the A/B reconstitution system. The contents of both syringes are mixed together immediately prior to dose delivery at or near the fracture site. After reconstitution, the contents are transferred into a graduated dosing syringe for delivery. The administered dosage forms will be a solution and will result in the dispersion of the compound with PLGH in NMP at desired strengths of, for example, 5 and 50 mgA/ml (mgA/ml refers to the free acid equivalent of the sodium salt form of the compound). The dosage form is a parenteral (e.g., subcutaneous, intramuscular or intramedullary) sustained release injection for local administration. This compound in a slow-release polymer matrix (depot injection) is designed for administration at or near a fracture site or bone defect or injury, and is not intended for intravenous administration. To provide adequate shelf-life stability for the dosage form, a two-syringe system (A/B), as described above, may be used, preferably with the sodium salt form of the compound. A uniphase formulation, preferably with the free acid form of the compound, is a preferred alternative formulation. Based on the compound and polymer stability, sterile filtration of the compound and irradiation of the polymer solution may be preferred for manufacturing a stable sterile product. In one embodiment, the dosage form can be manufactured and shipped as separate aluminum pouches containing syringes filled with the lyophile form of the compound in one pouch and the polymer solution in the other pouch. Delivery containers, systems and methods for the lyophilization of the bone growth promoting compounds of the present invention to prepare pharmaceutical compositions and kits are described in published International patent application, WO 01/73363, published 4 Oct. 2001, which is incorporated by reference herein.

EXAMPLES

The following examples are set forth as representative of the present invention. These examples are not to be construed as limiting the scope of the invention as these and other equivalent embodiments will be apparent in view of the present disclosure and accompanying claims.

Example A

To obtain dosage form at strengths of 5 and 50 mgA/ml, the following combinations A) and B) of lyophile and polymer syringe, respectively, were used:

A) 5 mgA/ml (upon reconstitution) of (3-(((4-tert-butyl-benzyl)-(pyridine-3-sulfonyl)-amino)-methyl)-phenoxy)-acetic acid, sodium salt formulation;

Drug Syringe A contained 4 mgA of the sodium salt lyophile in 1.25 ml male syringe without graduations; and Vehicle Syringe B contained 0.8 ml 50% RG502H/50% NMP solution in 1.25 ml female syringe without graduations.

B) 50 mgA/ml (upon reconstitution) of (3-(((4-tert-butyl-benzyl)-(pyridine-3-sulfonyl)-amino)-methyl)-phenoxy)-acetic acid, sodium salt formulation:

Drug Syringe A contained 40 mgA of the sodium salt lyophile in 1.25 ml male (fat) B-D syringe without graduations; and Vehicle Syringe B contained 0.8 ml 50% RG502H/50% NMP solution in 1.25 ml female (thin) syringe without graduations.

MgA refers to free acid equivalent of the sodium salt form of the compound;

The percentages used in these examples are based on the weight of the indicated ingredients;

RG502H is a PLGH copolymer with 1:1 ratio of lactic and glycolic acid with inherent viscosity of 0.2 dl/gm, which is commercially available such as from Boehringer Ingelheim as Copolymer RESOMER® RG 502H.

Example 1

50% RG502H/50% NMP with 5 mgA/ml of sodium salt of (3-(((4-tert-butyl-benzyl)-(pyridine-3-sulfonyl)-amino)-methyl)-phenoxy)-acetic acid, mixed A/B (polymer solution autoclaved, compound lyophilized)

Example 2

50% RG502H/50% NMP with 10 mgA/ml of sodium salt of (3-(((4-tert-butyl-benzyl)-(pyridine-3-sulfonyl)-amino)-methyl)-phenoxy)-acetic acid, mixed A/B (polymer solution irradiated, compound lyophilized)

Example 3

50% RG502H/50% NMP with 50 mgA/ml of sodium salt of (3-(((4-tert-butyl-benzyl)-(pyridine-3-sulfonyl)-amino)-methyl)-phenoxy)-acetic acid, mixed A/B (polymer solution irradiated, compound lyophilized)

Example 4

47% RG502H/3% PLG-PEG/50% NMP with 50 mgA/ml of sodium salt of (3-(((4-tert-butyl-benzyl)-(pyridine-3-sulfonyl)-amino)-methyl)-phenoxy)-acetic acid, uniphase

Example 5

47% RG503H/3% PLG-PEG/50% NMP with 50 mgA/ml of sodium salt of (3-(((4-tert-butyl-benzyl)-(pyridine-3-sulfonyl)-amino)-methyl)-phenoxy)-acetic acid, uniphase

Example 6

45% RG504H/55% NMP with 50 mgA/ml of sodium salt of (3-(((4-tert-butyl-benzyl)-(pyridine-3-sulfonyl)-amino)-methyl)-phenoxy)-acetic acid, uniphase

Example 7

37% RG503H/63% NMP with 50 mgA/ml of sodium salt of (3-(((4-tert-butyl-benzyl)-(pyridine-3-sulfonyl)-amino)-methyl)-phenoxy)-acetic acid, mixed A/B (polymer solution autoclaved, compound lyophilized)

Example 8

37% RG503H/63% NMP with 50 mgA/ml of sodium salt of (3-(((4-tert-butyl-benzyl)-(pyridine-3-sulfonyl)-amino)-methyl)-phenoxy)-acetic acid, mixed A/B (polymer solution irradiated, compound lyophilized)

Example 9

50% RG502H/50% NMP with 5 mgA/ml of (3-(((4-tert-butyl-benzyl)-(pyridine-3-sulfonyl)-amino)-methyl)-phenoxy)-acetic acid, uniphase Evaluation of Test Compounds in Controlled Release Formulations I. Rat Femoral Transverse Fracture Model Male Sprague-Dawley rats at 3 to 4 months of age were used. The animals were anesthetized with ketamine and xylazine at doses of 100 and 10 mg/kg, respectively. The right hindlimb of each rat was shaved and cleaned. A 1 cm incision was made just lateral to the patella and the femoral condyle was exposed. A Kirschner wire (0.045" in diameter) was introduced into the intramedullary canal through the intercondylar portion to serve as an internal stabilization. The muscle incision was closed with Vicryl® and the skin incision was closed with stainless steel wound clips. The mid-diaphysis of the pinned femur was fractured by means of a three-point bending device driven by a dropped weight. The rats were permitted full weight-bearing and unrestricted activity after awakening from anesthesia. The test agents were administered on various days after surgery by percutaneous injection onto the fracture site. The animals were sacrificed on various days after treatment and the femurs were collected for analysis. Fracture healing was evaluated by using radiography, histomorphometry and biomechanical test. (See, e.g., F. Bonnarens and T. A. Einhorn, "Production of a standard closed fracture in laboratory animal bone," Journal of Orthopaedic Research 2:97-101 (1984).)

II. Study Protocol and Results in the Rat Femoral Fracture Model

Male Sprague-Dawley rats at 3 to 4 months of age were subjected to right femoral fracture. The rats of control group were injected with respective vehicle. The rats in the treatment group received single dose of test compound in a controlled release formulation of the present invention by percutaneous injection to the fracture site immediately after surgery. The drug concentration was 50 mg/ml, injection volume was 300 ul, and the total dose was 15 mg/rat. The animals were sacrificed on day 21 and the femurs were collected for radiographic assessments. The femurs treated with the test compound had larger and denser calluses than those treated with vehicle as assessed by radiography. The data indicated that the test compound stimulated callus formation and may be effective in enhancing fracture healing.

The following are some examples of polymer formulations, which showed positive results in the Rat Femoral Fracture Model:

50% RG502H/50% NMP with 50 mgA/ml of sodium salt of (3-(((4-tert-butyl-benyl)-(pyridine-3-sulfonyl)-amino)-methyl)-phenoxy)-acetic acid, mixed A/B (polymer solution irradiated, compound lyophilized);

47% RG502H/3% PLG-PEG/50% NMP with 50 mgA/ml of sodium salt of (3-(((4-tert-butyl-benyl)-(pyridine-3-sulfonyl)-amino)-methyl)-phenoxy)-acetic acid, uniphase;

47% RG503H/3% PLG-PEG/50% NMP with 50 mgA/ml of sodium salt of (3-(((4-tert-butyl-benyl)-(pyridine-3-sulfonyl)-amino)-methyl)-phenoxy)-acetic acid, uniphase.

MgA refers to free acid equivalent of the sodium salt form of the compound;

RG502H is a PLGH copolymer with 1:1 ratio of lactic and glycolic acid with an inherent viscosity of 0.2 dl/gm, which is commercially available such as from Boehringer Ingelheim as Copolymer RESOMER® RG 502H;

RG503H is a PLGH copolymer with 1:1 ratio of lactic and glycolic acid with an inherent viscosity of 0.3 dl/g, which is commercially available such as from Boehringer Ingelheim as Copolymer RESOMER® RG 503H.

III. Rat Periosteal Injection Model

Male Sprague-Dawley rats at 3 weeks of age were used. The rats were anesthetized with isoflurane inhalation (2-3 minutes) in a conduction chamber located in a fume hood. The right hindlimb of each rat was shaved and cleaned. A 25 G needle attached with a Hamilton syringe pre-filled with testing solution was used for the local injection. The solution was injected onto the subperiosteum of the anterior, mid-diaphyseal region of femur in a volume of 5 to 10 ul for various days. On day 15, the rats were sacrificed and the femurs were collected for analysis. (See, e.g., M. E. Joyce, A. B. Roberts, M. B. Sporn and M. Bolander, "Transforming growth factor-β and the initiation of chondrogenesis and osteogenesis in the rat femur," The Journal of Cell Biology 110:2195-2207 (1990).)

IV. Study Protocol and Results in the Rat Periosteal Injection Model

On day one, the right femurs of male Sprague-Dawley rats received single injection of vehicle or test compound in a polymer formulation. The test compound was the sodium salt of (3-(((4-tert-butyl-benzyl)-(pyridine-3-sulfonyl)-amino)-methyl)-phenoxy)-acetic acid. On day 15, all rats were sacrificed and the right femurs were collected for analysis. Periosteal bone induction was assessed by using radiography and dual-energy X-ray absorptiometry (DEXA). Radiography showed new bone formation located on the anterior aspect of the right femurs treated with the test compound. The bone mineral content (BMC) of the injected region of the femur (area between lesser trochanter and mid-shaft of the femur) as assessed by DEXA was significantly increased in the rats treated with the test compound as compared with those treated with vehicle (see some examples of these formulations listed in Table A below).

TABLE A

| Formulation | Drug Load (mgA/ml) | X-Ray efficacy (positive/total #) | BMC (% increase vs. Veh) |
|---|---|---|---|
| 47% 50:50 PLGH (RG502H Grade) + 3% PLG-PEG (IV = 0.79 dL/g)/50% NMP | 0 | 0/10 | |
| 37% PLGH (RG503H Grade)/63% NMP | 0 | 0/10 | |
| 47% 50:50 PLGH (RG502H Grade) + 3% PLG-PEG (IV = 0.79 dL/g)/50% NMP | 50 | 9/10 | +21 |
| 47% 50:50 PLGH (RG503H Grade) + 3% PLG-PEG (IV = 0.79 dL/g)/50% NMP | 50 | 9/10 | +23 |
| 45% 50:50 PLGH (RG504H Grade)/55% NMP | 50 | 10/10 | +19 |
| 45% 50:50 PLGH (RG502H Grade)/5% PLG-PEG/50% NMP | 50 | 8/9 | +26 |
| 50% 50:50 PLGH (RG502H Grade)/50% NMP | 50 | 5/9 | +19 |
| 37% 50:50 PLGH (RG503H Grade)/63% NMP | 50 | 7/9 | +15 |
| 45% 50:50 PLGH (RG502H Grade)/5% PLG-PEG/50% NMP | 5 | 9/10 | +18 |
| 47% PLGH (RG503H Grade) + 3% PLG-PEG/50% NMP | 5 | 6/8 | +18 |

Efficacy of Test Compound in a Slow-Release Matrix Formulation in Dog Segmental Defect Model The ulnar segmental defect model was used to test the efficacy of a single dose of the test compound (which was the sodium salt of (3-(((4-tert-butyl-benzyl)-(pyridine-3-sulfonyl)-amino)-methyl)-phenoxy)-acetic acid) in a PLGH formulation (50% 50:50 PLGH (RG502H Grade)/50% NMP). The protocol was modified as follows: With animals under general anesthesia, the foreleg was prepped and draped in sterile fashion. A lateral incision approximately 10 cm in length was made and the ulna was exposed extraperiostally. Periosteum was cut and moved to the proximal and distal parts of the incision. Then a 1.5 cm segmental defect was made in the midulna using a pendular saw. The radius and the remaining interosseal membrane were left intact. The defect site was irrigated with saline to remove bone debris. The site was then filled with test compound in a slow-release matrix formulation, as described above. The dogs were divided into the following groups.

TABLE 1

| Groups | Treatment |
|---|---|
| A | 1 ml of carrier |
| B | 50 mg of test compound (1 ml of 50 mg/ml formulation). |
| C | 10 mg of test compound (1 ml of 10 mg/ml formulation). |
| D | 10 mg of test compound (0.2 ml of 50 mg/ml formulation). |

Radiographs of the forelimbs were obtained immediately following surgery and every two weeks thereafter until the termination of the study. Radiographs were graded on a 0 to 6 scale (Table 2).

TABLE 2

| Radiographic Grading Scale | |
|---|---|
| Grade 0 | No change from immediate postoperative appearance |
| Grade 1 | Trace of radiodense material in defects |
| Grade 2 | Flocculent radiodensity with flecks of calcification and no defect bridging |
| Grade 3 | Defect bridged at least one point with material of nonuniform radiodensity |

TABLE 2-continued

| Radiographic Grading Scale | |
|---|---|
| Grade 4 | Defect bridged in medial and lateral sides with material of uniform radiodensity, cut ends of cortex remain visible |
| Grade 5 | Same as Grade 3, at least one of four cortices obscured by new bone |
| Grade 6 | Defect bridged by uniform new bone, cut ends of cortex not seen |

It was observed that a single application of test compound in a slow release matrix formulation induced complete rebridgement in dogs present in groups B, C and D. The newly formed bone remodeled back to the same shape and size as the contralateral bone by week 24. Even after 24 weeks, ulna treated with vehicle did not show any healing as assessed by radiography.

Similar results were obtained when the dogs were treated with either 10 mg of the 50 mg/ml (0.2 ml final volume) of the test compound or with 1 ml of the 10 mg/ml formulation (groups C and D). Overall between 70-75% of the treated animals healed compared to none for the vehicle treated controls (Table 3).

TABLE 3

Results from the Dog Segmental Defect Model

| Groups | Radiographic Scale | Complete rebridging/number of dogs |
|---|---|---|
| A | Very Poor healing. Radiographic Scale between 0 and 1 | 0/8 |
| B | Radiographic scale between 5 and 6 for two dogs. The other two were between 1 and 2. | 2/4 |
| C | Scale of 5 to 6 for 9 dogs. Scale of 1 to 2 for one dog. Two dogs did not respond. | 9/12 |
| D | Scale of 5 to 6. One dog did not respond. | 3/4 |

When the test compound (50 mg/ml) was tested in the above model in a formulation containing 50% 50:50 PLGH (RG503H Grade)/50% NMP, it did not work well. Union was achieved in some dogs, but it was delayed compared to dogs treated with the formulation containing the RG502H Grade of PLGH.

The Canine Tibial Osteotomy Model

Normal fracture healing usually represents a biologically optimum healing process, as a result detecting an acceleration of healing in pre-clinical models that heal rapidly is both difficult and challenging. The test compound (which was the sodium salt of (3-(((4-tert-butyl-benzyl)-(pyridine-3-sulfonyl)-amino)-methyl)-phenoxy)-acetic acid) in a PLGH formulation (50% 50:50 PLGH (RG502H Grade)/50% NMP) was studied to determine its effect on accelerating healing in a rapidly healing canine osteotomy model. Enhancement of healing in this model supports potential applications of the test compound to heal normal fractures in humans since humans tend to heal fractures more slowly.

Beagle male dogs 12±3 kg, 14 months of age were used for the study. Dogs were divided into four groups of three to four animals each.

TABLE 4

| Groups | Treatment |
|---|---|
| A | No treatment |
| B | 0.5 ml carrier |
| C | 5 mg of test compound (0.5 ml of 10 mg/ml formulation). |
| D | 25 mg of test compound (0.5 ml of 50 mg/ml formulation). |

With animals under general anesthesia, the hindleg was prepped and draped in sterile fashion. A lateral incision approximately 4 cm in length was made. Surgical osteotomy was made on the distal portion of the dog tibia using a Gigli saw. The defect was stabilized using an AO plate. The fibula and the remaining interosseal membrane was left intact and the defect site was irrigated with saline to remove bone debris. The site was then filled with carrier as described above. Following surgery, animals were allowed full weight-bearing activity, and water and food ad libitum. Radiographs of the hindlimbs were obtained immediately following surgery and every two weeks thereafter until the termination of the study. Radiographs were graded on a 0 to 6 scale.

TABLE 5

Results from the Dog Tibial Osteotomy Study

| Groups | Radiographic Scale | Rebridging/number of dogs |
|---|---|---|
| A | Between 2 to 3. | 0/3 |
| B | Between 2 to 3. | 0/3 |
| C | Between 4 to 5. | 4/4 |
| D | Between 4 to 5. | 3/4 |

None of the four dogs rebridged the defect area within the time frame of 8 weeks in groups A and B. This timing was chosen for the termination of the study to obtain differences between treated groups of animals. Four out of four animals showed significant rebridgement within the time period of 8 weeks in group C. In group D, one animal was a non-responder, however, the other three showed significant healing (Table 5).

The invention claimed is:

1. A method of forming an in-situ, in a living body, comprising the steps of:
   (a) dissolving a non-reactive, water-insoluble biodegradable polymer in a biocompatible, highly water soluble organic solvent that is dispersible in body fluid in situ to form a flowable composition;
   (b) adding an effective amount of a compound to the flowable composition to provide a pharmaceutical composition;
   (c) placing the pharmaceutical composition within the body; and
   (d) allowing the to dissipate to produce a solid or gel implant which releases the compound by diffusion, erosion or a combination of diffusion and erosion as the implant biodegrades;
   wherein the compound or a pharmaceutically acceptable salt thereof is selected from the group consisting of:
   (3-(((4-tert-butyl-benzyl)-(pyridine-3-sulfonyl)-amino)-methyl)-phenoxy)-acetic-acid;
   7-[(4-butyl-benzyl)-methanesulfonyl-amino]-heptanoic acid; and
   7-{[2-(3,5-dichloro-phenoxyl)-ethyl]-methanesulfonyl-amino}-heptanoic acid;

wherein the polymer is selected from the group consisting of polylactides and copolymers, thereof with glycolide; and wherein the solvent is N-methyl-2-pyrrolidone (NMP).

2. A method of claim 1 wherein the copolymer is poly-lactic-co-glycolic acid (PLGH).

3. A method of claim 1 further comprising delivering said liquid in-situ through a syringe.

4. A method of claim 1 wherein the implant is formed at or near a bone fracture, bone defect or bone injury in the body.

5. The method of claim 4 wherein the copolymers poly-lactic-co-glycolic acid (PLGH).

6. The method of claim 5 wherein the ratio of lactic acid to glycolic acid in the poly-lactic-co-glycolic acid (PLGH) copolymer is about 1 to about 1.

7. The method of claim 6 wherein the compound is (3-(((4-tert-butyl-benzyl)-(pyridine-3-sulfonyl)-amino)-methyl)-phenoxy)-acetic acid or a pharmaceutically acceptable salt thereof.

8. The method of claim 7 wherein the (3-(((4-tert-butyl-benzyl)-(pyridine-3-sulfonyl)-aminol)-methy)-phenoxy)-acetic acid or a pharmaceutically acceptable salt thereof is in lyophilized form.

9. The method of claim 8 wherein the wherein the weight percentage of PLGH to NMP in solution is selected from the following:

about 37% PLGH to about 63% NMP; about 45% PLGH to about 55% NMP;

about 50% PLGH to about 50% NMP; and about 55% PLGH to about 45% NMP.

10. The method of claim 9 wherein the weight percentage of PLGH to NMP in solution is about 50° PLGH to about 50% NMP.

* * * * *